(12) United States Patent
Srinivas et al.

(10) Patent No.: US 7,754,643 B2
(45) Date of Patent: Jul. 13, 2010

(54) TRANSESTERIFICATION CATALYST AND A PROCESS FOR THE PREPARATION THEREOF

(75) Inventors: Darbha Srinivas, Pune (IN); Rajendra Srivastava, Pune (IN); Paul Ratnasamy, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 11/394,133

(22) Filed: Mar. 30, 2006

(65) Prior Publication Data

US 2007/0093380 A1 Apr. 26, 2007

(30) Foreign Application Priority Data

Oct. 7, 2005 (IN) .................... 2723/DEL/2005

(51) Int. Cl.
*B01J 27/26* (2006.01)
*B01J 31/00* (2006.01)

(52) U.S. Cl. .................. 502/175; 502/200; 502/159; 502/150; 502/152; 502/156; 502/172

(58) Field of Classification Search ............. 502/175, 502/200, 159, 150, 152, 156, 172
See application file for complete search history.

(56) References Cited

U.S. PATENT DOCUMENTS

| 3,278,457 | A | | 10/1966 | Milgrom |
| 5,482,908 | A | * | 1/1996 | Le-Khac ............... 502/156 |
| 5,536,883 | A | * | 7/1996 | Le-Khac ............... 568/620 |
| 5,578,090 | A | | 11/1996 | Bradin |
| 5,713,965 | A | | 2/1998 | Foglia et al. |
| 6,015,440 | A | | 1/2000 | Noureddini |
| 6,398,707 | B1 | | 6/2002 | Wu et al. |
| 6,399,800 | B1 | | 6/2002 | Haas et al. |
| 6,479,689 | B1 | | 11/2002 | Tojo et al. |
| 6,624,286 | B2 | | 9/2003 | Hofmann et al. |
| 6,642,399 | B2 | | 11/2003 | Boocock |
| 6,696,583 | B2 | | 2/2004 | Koncar et al. |
| 6,712,867 | B1 | | 3/2004 | Boocock |
| 6,822,105 | B1 | | 11/2004 | Luxem et al. |
| 6,835,858 | B1 | | 12/2004 | De Jonge et al. |
| 6,855,838 | B2 | | 2/2005 | Haas et al. |
| 7,211,681 | B2 | | 5/2007 | Furuta |
| 2004/0044240 | A1 | * | 3/2004 | Grosch et al. ............ 558/277 |
| 2005/0027137 | A1 | | 2/2005 | Hooker |
| 2007/0004599 | A1 | | 1/2007 | Darbha et al. |
| 2007/0083056 | A1 | | 4/2007 | Srinivas et al. |
| 2007/0083062 | A1 | | 4/2007 | Srinivas et al. |
| 2007/0093380 | A1 | | 4/2007 | Srinivas et al. |
| 2007/0167642 | A1 | | 7/2007 | Oku et al. |

FOREIGN PATENT DOCUMENTS

WO 00/05327 2/2000
WO 2004/048311 6/2004

OTHER PUBLICATIONS

European Office Communication for EP Patent Application No. 06 011 066.5-2104, mailed Jan. 31, 2007, 2 pages.
European Office Communication for EP Patent Application No. 06 011 066.5-2104, mailed Apr. 10, 2007, 2 pages.
European Search Report for EP Patent Application No. 06 011 066.5-2104, mailed Oct. 18, 2006, 1 pages.

* cited by examiner

*Primary Examiner*—Elizabeth D Wood
(74) *Attorney, Agent, or Firm*—Meyertons, Hood, Kivlin, Kowert & Goetzel, P.C.; Eric B. Meyertons

(57) ABSTRACT

The present invention provides a novel transesterification catalyst having the general formula:

$$Zn_3M_2(CN)_n(ROH) \cdot xZnCl_2 \cdot yH_2O$$

wherein R is tertiary-butyl and M is a transition metal ion selected from Fe, Co and Cr, x varies from 0 to 0.5, y varies from 3-5 and n is 10 or 12.

The above said catalyst is useful for an efficient transesterification of glycerides, fatty acid esters and cyclic carbonates on reactions with alcohols.

6 Claims, No Drawings

TRANSESTERIFICATION CATALYST AND A PROCESS FOR THE PREPARATION THEREOF

FIELD OF THE INVENTION

The present invention relates to a novel transesterification catalyst and a process for the preparation thereof. The present invention also relates to a process for transesterification using these catalysts. More particularly, it relates to a solid double metal cyanide transesterification catalyst having the general formula:

$$Zn_3M_2(CN)_n(ROH).xZnCl_2.yH_2O$$

wherein R is tertiary butyl and M is a transition metal ion selected from Fe, Co and Cr; x varies from 0 to 0.5, y varies from 3-5 and n is 10 or 12.

BACKGROUND OF THE INVENTION

Transesterification is a crucial step in several industrial processes such as (i) production of higher acrylates from methylmethacrylate (for applications in resins and paints), (ii) polyethylene terephthalate (PET) from dimethyl terephthalate (DMT) and ethylene glycol (in polyester manufacturing), (iii) intramolecular transesterifications leading to lactones and macrocycles, (iv) alkoxy esters (biodiesel) from vegetable oils, and (v) co-synthesis of dimethyl carbonate (an alkylating agent, octane booster and precursor for polycarbonates) and ethylene glycol from ethylene carbonate and methanol (U. Schuchardt et al., J. Braz. Chem. Soc. 9 (1998) 199). Acids and bases are known to accelerate the rate of transesterifications (J. Otera Chem. Rev. 93 (1993) 1449). Other than mineral acids and bases, compounds like metal alkoxides (aluminum isopropoxide, tetraalkoxytitanium, $(RO)Cu(PPh_3)_{sub.n}$, $PdMe(OCHCF_3Ph(dpe))$, organotin alkoxides etc.), non-ionic bases (amines, dimethylaminopyridine, guanidines etc.) and lipase enzymes also catalyze these transformations (J. Otera Chem. Rev. 93 (1993) 1449).

Alkaline metal alkoxides (as CH.sub.3ONa for the methanolysis) are the most active catalysts, since they give very high yields (>98%) of fatty acid alkyl esters in transesterification of triglycerides with alcohols in short reaction times (30 mm) even if they are applied at low molar concentrations (0.5 mol %) (J. Food Composition and Analysis Year 2000, Vol. 13, pages 337-343). However, they require high quality oil and the absence of water, which makes them inappropriate for typical industrial processes (J. Braz. Chem. Soc. Vol. 9, No. 1, Year 1998, pages 199-210). Alkaline metal hydroxides (NaOH and KOH) are cheaper than metal alkoxides but require increasing catalyst concentration (1-2 mol %). NaOH is more superior to KOH as the latter and other alkali hydroxides yield more saponified products than the biodiesel.

Recently, enzymatic transesterification using lipase has become more attractive for transesterification of triglycerides, since the glycerol produced as a by-product can easily be recovered and the purification of fatty acid esters is simple to accomplish. (J. Mol. Catal. B: Enzymatic Vol. 17, Year 2002, pages 133-142).

Use of immobilized lipases in the synthesis of fatty acid methyl esters from sunflower and soybean oils were reported by Soumanou and Bornscheuer and Watanabe et al (Enzy. Microbiol. Tech. Vol. 33, Year 2003, page 97; J. Mol. Catal. B: Enzymatic Vol. 17, Year 202, pages 151-155). They found that the immobilized enzyme is active at least for 120 h during five batch runs without significant loss of activity. Among the various lipases investigated the enzyme from *Pseudomonas fluorescens* (Amano AK) exhibited the highest conversion of oil. Khare and Nakajima (Food Chem. Vol. 68, Year 2000, pages 153-157) also reported the use of immobilized lipase enzyme.

U.S. Pat. No. 5,713,965 describes the production of biodiesel, lubricants and fuel and lubricant additives by transesterification of triglycerides with short chain alcohols in the presence of an organic solvent such as an alkane, arene, chlorinated solvent, or petroleum ether using *Mucor miehei* or *Candida Antarctica*-derived lipase catalyst. Patents Nos. WO 00/05327 A1, WO 02/28811 A1, WO 2004/048311 A1, WO 2005/021697 A1 and WO 2005/016560 A1 and U.S. Pat. Nos. 5,578,090; 6,855,838; 6,822,105; 6,768,015; 6,712,867; 6,642,399; 6,399,800; 6,398,707; 6,015,440 also teach us the production fatty acid alkyl esters using either lipase catalysts or metal ion catalysts. Patent No. WO 2004/085583 A1 describes transesterification of fats with methanol and ethanol in the presence of a solid acid catalyst having ultrastrong-acid properties in a short time at around ordinary pressure.

Replacement of homogeneous catalyst by a solid catalyst eliminates the processing costs. At the end of the reaction, the solid catalyst can be recovered by simple filtration from the product mixture and reused. Leclercq et al. (J. Am. Oil. Chem. Soc. Vol 78, Year 2001, page 1161) studied the transesterification of rapeseed oil in the presence of Cs-exchanged NaX and commercial hydrotalcite (KW2200) catalysts. At a high methanol to oil ratio of 275 and 22 h reaction time at methanol reflux, the Cs-exchanged NaX gave a conversion of 70% whereas 34% conversion was obtained over hydrotalcite. ETS-4 and ETS-10 catalysts gave conversions of 85.7% and 52.7%, respectively at 220° C. and 1.5 h reaction time (U.S. Pat. No. 5,508,457). Suppes et al (J. Am. Oil. Chem. Soc. Vol. 78, Year 2001, page 139) achieved a conversion of 78% at 240° C. and >95% at 160° C. using calcium carbonate rock as catalyst. Of late, Suppes et al reported the use of Na, K and Cs exchanged zeolite X, ETS-10, NaX occluded with $NaO_x$ and sodium azide in the transesterification of soybean oil with methanol (Appl. Catal. A: Gen. Vol. 257, Year 2004, page 213). Furuta et al (Catal. Commun. Vol. 5, Year 2004, pages 721-723) tell transesterification of soybean oil with methanol at 200-300° C. using solid superacid catalysts of sulfated tin and zirconium oxides. Use of tin complexes immobilized in ionic liquids for vegetable oil alcoholysis was reported by Abreu et al (J. Mol. Catal. A: Chem. Vol. 227, Year 2005, pages 263-267; J. Mol. Catal. A: Chem. Vol. 209, Year 2004, pages 29-33). Kim et al reported the use of heterogeneous base catalysts ($Na/NaOH/Al_2O_3$) for the methanolysis of vegetable oils. More efficient reusable solid catalyst for transesterifications is highly desirable.

The present invention eliminates the drawbacks of the prior-art processes. It deals with preparation of a transesterification catalyst which comprises reacting an aqueous $ZnCl_2$ solution, an aqueous $K_4Fe(CN)_6$ solution and a tri-block copolymer poly(ethylene glycol)-block-poly(propylene glycol)-block-poly(ethylene glycol) ($EO_{20}$-$PO_{70}$-$EO_{20}$; molecular weight of about 5800) dissolved in tert.-butanol at ambient conditions, separating the solid catalyst and drying. Co-existence of Zn and Fe in the active site linking through cyano bridges makes it efficient for transesterification reactions. The catalyst could be separated easily by centrifugation or by simple filtration and reused. Unlike the prior-art catalysts no leaching of metal ions into the reaction mixture was observed with the catalysts of the present invention. Most importantly, the catalyst is highly efficient and only a small amount (1 wt % of oil) is needed to carryout the reaction at moderate conditions.

OBJECTIVES OF THE INVENTION

The main objective of the present invention is to provide an efficient, reusable, heterogeneous catalyst for transesterification reactions.

Another objective is to provide a process for the preparation of an efficient, reusable, heterogeneous catalyst for transesterification reactions.

SUMMARY OF THE INVENTION

In the investigations leading to the present invention, it was found that the double metal cyanide catalysts are highly efficient and could be easily separated from the products for further reuse. The prior art catalysts, mineral acid, alkali bases and lipases need additional expenses for catalyst separation. An easily separable catalyst system e.g., the catalyst of the present invention is beneficial and possibly leads to an economical and eco-friendly process. Hence, the solid catalysts of the present invention are not only efficient but avoid the tedious process of catalyst recovery characteristic of most of the prior art catalysts.

Accordingly, the present invention provides novel transesterification catalyst having the general formula:

$$Zn_3M_2(CN)_n(ROH).xZnCl_2.yH_2O$$

wherein R is tertiary-butyl and M is a transition metal ion selected from Fe, Co and Cr, x varies from 0 to 0.5, y varies from 3-5 and n is 10 or 12.

In an embodiment of the present invention the catalyst comprises $Zn^{2+}$ and $Fe^{2+}$ ions bridged through cyanide groups.

In yet another embodiment the catalyst has following characteristics:

| | |
|---|---|
| Total surface area ($S_{BET}$) | 35-40 $m^2/g$ |
| External surface area ($S_{Exm.}$) | 22-25 $m^2/g$ |
| Micropore area | 14-18 $m^2/g$ |
| Average pore diameter | 3-5 nm |
| Total pore volume | 0.03-0.04 cc/g |
| % C-content | 23-25 |
| % H-content | 2.2-2.9 |
| % N-content | 17-18 |
| Morphology (SEM): | Spherical shaped particles |

In yet another embodiment the cation transesterification catalyst obtained is useful for an efficient transesterification of glycerides, fatty acid esters and cyclic carbonates on reactions with alcohols.

In yet another embodiment the catalyst reusable in several recycling transesterification experiments without significant loss in activity The present invention further provides a process for the preparation of a novel transesterification catalyst having the general formula:

$$Zn_3M_2(CN)_n(ROH).xZnCl_2.yH_2O$$

wherein R is tertiary-butyl and M is a transition metal ion selected from Fe, Co and Cr, x varies from 0 to 0.5, y varies from 3-5 and n is 10 or 12 transesterification catalyst, the said process comprising the steps of:

a) dissolving $ZnCl_2$ in a mixture of water and tertiary butanol,
b) adding the above said solution obtained in step (a) to an aqueous solution of $K_4Fe(CN)_6$, under stirring,
c) adding tri-block copolymer poly(ethyleneglycol)-block-poly(propylene glycol)-block-poly(ethyleneglycol) ($EO_{20}$-$PO_{70}$-$EO_{20}$; molecular weight of about 5800) dissolved in a mixture of tert.-butanol and water to the above said resultant mixture obtained in step (b), under stirring, at a temperature in the range of 25-70 C,
d) filtering the above said reaction mixture obtained in step (c) to obtain a solid product, followed by washing with distilled water and drying it at 20-50° C. and
e) activating the above said dried solid product, at a temperature in the range of 150-200.degree. C. to obtained the desired transesterification catalyst.

In yet another embodiment the catalyst comprises $Zn^{2+}$ and $Fe^{2+}$ ions bridged through cyanide groups.

In yet another embodiment in step (a) the concentration of tertiary butanol in water used is in the range of 20-30% (v/v).

In yet another embodiment in step (c) the concentration of tri-block copolymer poly(ethyleneglycol)-block-poly(propylene glycol)-block-poly(ethyleneglycol) in a mixture of water and tertiary butanol used is in the range of 30-40% (w/v).

In yet another embodiment in step (c) the ratio of tertiary butanol to water in a mixed solvent mixture used is in the range of 20:1 to 30:1 (v/v).

In yet another embodiment the catalyst obtained is useful for an efficient transesterification of glycerides, fatty acid esters and cyclic carbonates on reactions with alcohols.

In still another embodiment the catalyst obtained is reusable in several recycling transesterification experiments without significant loss in activity.

The present invention is illustrated herein below with examples, which are illustrative only and should not be construed to limit the scope of the present invention in any manner.

EXAMPLE 1

This example illustrates the preparation of the Fe—Zn double metal cyanide catalyst of the present invention. In a typical catalyst preparation, $K_4[Fe(CN)_6]$ (0.01 mol) was dissolved in double distilled water (40 ml) (Solution-1). $ZnCl_2$ (0.1 mol) was dissolved in a mixture of distilled water (100 ml) and tertiary-butanol (20 ml) (Solution-2). Poly(ethylene glycol)-block-poly(propylene glycol)-block-poly(ethylene glycol) ($EO_{20}$-$PO_{70}$-$EO_{20}$; molecular weight of about 5800) (15 g) was dissolved in a mixture of 2 ml of distilled water and 40 ml of tertiary-butanol (Solution-3). Solution-2 was added to solution-1 over 60 min at 50° C. with vigorous stirring. White precipitation occurred during the addition. Then, solution-3 was added to the above reaction mixture over a period of 5 min and stirring was continued for further 1 h. The solid formed was filtered, washed with distilled water (500 ml) and dried at 25° C. This material was activated at 180-200° C. for 4 h prior to using it in the reactions.

EXAMPLE 2

This example illustrates the preparation of the Fe—Zn double metal cyanide catalyst of the present invention. In a typical catalyst preparation, $K_4[Fe(CN)_6]$ (0.01 mol) was dissolved in double distilled water (40 ml) (Solution-1). $ZnCl_2$ (0.1 mol) was dissolved in a mixture of distilled water (100 ml) and tertiary-butanol (20 ml) (Solution-2). Poly(ethylene glycol)-block-poly(propylene glycol)-block-poly(ethylene glycol) (E0$_{20}$-PO$_{70}$-EO$_{20}$; molecular weight of about 5800) (15 g) was dissolved in a mixture of 2 ml of distilled water and 40 ml of tertiary-butanol (Solution-3). Solution-2 was added to solution-1 over 60 min at 70° C. with vigorous stirring. White precipitation occurred during the addition. Then, solution-3 was added to the above reaction mixture over a period of 5 min and stirring was continued for further 1 h. The solid formed was filtered, washed with distilled water (500 ml) and dried at 100° C. This material was activated at 180-200° C. for 4 h prior to using it in the reactions.

EXAMPLE 3

This example illustrates the preparation of the Fe—Zn double metal cyanide catalyst of the present invention. In a typical catalyst preparation, K$_3$[Fe(CN)$_6$] (0301 mol) was dissolved in double distilled water (40 ml) (Solution-1). ZnCl$_2$ (0.1 mol) was dissolved in a mixture of distilled water (100 ml) and tertiary-butanol (20 ml) (Solution-2). Poly(ethylene glycol)-block-poly(propylene glycol)-block-poly(ethylene glycol) (E0$_{20}$-PO$_{70}$-EO$_{20}$; molecular weight of about 5800) (15 g) was dissolved in a mixture of 2 ml of distilled water and 40 ml of tertiary-butanol (Solution-3). Solution-2 was added to solution-1 over 60 min at 50° C. with vigorous stirring. White precipitation occurred during the addition. Then, solution-3 was added to the above reaction mixture over a period of 5 min and stirring was continued for further 1 h. The solid formed was filtered, washed with distilled water (500 ml) and dried at 25° C. This material was activated at 180-200° C. for 4 h prior to using it in the reactions.

EXAMPLE 4

This example illustrates the preparation of the Fe—Co double metal cyanide catalyst of the present invention. In a typical catalyst preparation, K$_4$[Co(CN)$_6$] (0.01 mol) was dissolved in double distilled water (40 ml) (Solution-1). ZnCl$_2$ (0.1 mol) was dissolved in a mixture of distilled water (100 ml) and tertiary-butanol (20 ml) (Solution-2). Poly(ethylene glycol)-block-poly(propylene glycol)-block-poly(ethylene glycol) (E0$_{20}$-PO$_{70}$-EO$_{20}$; molecular weight of about 5800) (15 g) was dissolved in a mixture of 2 ml of distilled water and 40 ml of tertiary-butanol (Solution-3). Solution-2 was added to solution-1 over 60 min at 50° C. with vigorous stirring. White precipitation occurred during the addition. Then, solution-3 was added to the above reaction mixture over a period of 5 min and stirring was continued for further 1 h. The solid formed was filtered, washed with distilled water (500 ml) and dried at 25° C. This material was activated at 180-200° C. for 4 h prior to using it in the reactions.

EXAMPLE 5

This example illustrates the preparation of the Fe—Co double metal cyanide catalyst of the present invention. In a typical catalyst preparation, K$_3$[Co(CN)$_6$] (0.01 mol) was dissolved in double distilled water (40 ml) (Solution-1). ZnCl$_2$ (0.1 mol) was dissolved in a mixture of distilled water (100 ml) and tertiary-butanol (20 ml) (Solution-2). Poly(ethylene glycol)-block-poly(propylene glycol)-block-poly(ethylene glycol) (E0$_{20}$-PO$_{70}$-EO$_{20}$; molecular weight of about 5800) (15 g) was dissolved in a mixture of 2 ml of distilled water and 40 ml of tertiary-butanol (Solution-3). Solution-2 was added to solution-1 over 60 min at 50° C. with vigorous stirring. White precipitation occurred during the addition. Then, solution-3 was added to the above reaction mixture over a period of 5 min and stirring was continued for further 1 h. The solid formed was filtered, washed with distilled water (500 ml) and dried at 25° C. This material was activated at 180-200° C. for 4 h prior to using it in the reactions.

EXAMPLE 6

This example describes the preparation of fatty acid methyl esters by transesterification of coconut oil with methanol using the transester catalyst double metal cyanide Fe—Zn. In a typical reaction, commercial coconut oil (5 g), methanol (oil:methanol molar ratio=1:6) and double metal cyanide catalyst (50 mg; 1 wt % of oil) were charged into a 100 ml stainless steel autoclave having a teflon-liner. The autoclave was closed and placed in a rotating synthesis reactor (Hiro Co., Japan, Mode—KU 02; rotating speed=30 rpm) and the reaction was conducted at autogenous pressure at 170 C for 4 h. It was then allowed to cool to 25 C.

First, catalyst was separated by centrifugation/filtration from the reaction mixture. Then, by vacuum distillation unreacted alcohol in the reaction mixture was removed. Pet ether (60 ml) and methanol (20 ml) were added to separate out the glycerol by-product from the reaction mixture. The methanol layer containing glycerol by-product was separated. This process of glycerol separation was repeated 2-3 times. Glycerol was isolated by distilling out methanol under vacuum. Later, the ether portion was distilled out to obtain the esterified products. A portion of the esterified products (100 mg) was diluted with dichloromethane (1 g) for analysis by gas chromatography. The products were identified by GC-MS.

EXAMPLE 7

This example illustrates the preparation of fatty acid methyl esters by transesterification of sunflower oil with methanol using the transester catalysts of the present invention. In a typical reaction, commercial sunflower oil (5 g), methanol (oil:methanol molar ratio=1:6) and double metal cyanide Fe—Zn catalyst (50 mg; 1 wt % of oil) were charged into a 100 ml stainless steel autoclave having a teflon-liner. The autoclave was closed and placed in a rotating synthesis reactor (Hiro Co., Japan, Mode—Ku 02; rotating speed=30 rpm) and the reaction was conducted at autogenous pressure at 170 C for 4 h. It was then allowed to cool to 25 C. The products were isolated by distillation and analyzed by gas chromatography.

EXAMPLE 8

This example describes the preparation of fatty acid methyl esters by transesterification of soybean oil with methanol using the transester catalyst of the present invention. In a typical reaction, soybean oil (5 g), methanol (oil:methanol molar ratio=1:6) and double metal cyanide Fe—Zn catalyst (50 mg; 1 wt % of oil) were charged into a 100 ml stainless steel autoclave having a teflon-liner. The autoclave was then placed in a rotating synthesis reactor (Hiro Co., Japan, Mode—KR 02; rotating speed=30 rpm) and the reaction was conducted at autogenous pressure at 170 C for 4 h. It was then allowed to cool to 25 C. The products were isolated by distillation and analyzed by gas chromatography.

EXAMPLE 9

This example describes transesterification of margarine oil with n-octanol using the transester catalyst of the present invention. In a typical reaction, margarine oil (5 g), n-octanol (oil:alcohol molar ratio=1:6) and double metal cyanide Fe—Zn catalyst (50 mg; 1 wt % of oil) were charged into a 100 ml stainless steel autoclave having a teflon-liner. The autoclave was then placed in a rotating synthesis reactor (Hiro Co., Japan, Mode—KH 02; rotating speed=30 rpm) and the reaction was conducted at 170° C. for 4 h. It was then allowed to cool to 25° C. The products were isolated by distillation and analyzed gas chromatography.

EXAMPLE 10

This example illustrates the preparation of dimethyl carbonate by transesterification of propylene carbonate with methanol using the transester catalyst of the present invention. In a typical transesterification reaction, propylene carbonate (1.02 g; 10 mmol), methanol (100 mmol), catalyst (250 mg) were charged in a 100 ml hydrothermal reactor. The reaction was carried out at 170 C for 8 h. The contents were allowed to cool to room temperature. Catalyst was separated by filtration from the reaction mixture. Then, the alcohol was removed from reaction mixture by distillation. The products were isolated by column chromatography (using pet ether: dichloromethane=1:1 and then with dichloromethane:methanol=95:5). The products were also analyzed by gas chromatography and identified by $^1$H NMR, FT-IR and GC-MS.

EXAMPLE 11

This example illustrates the preparation of diethyl carbonate by transesterification of propylene carbonate with ethanol using the transester catalyst of the present invention. In a typical transesterification reaction, propylene carbonate (1.02 g; 10 mmol), ethanol (100 mmol), catalyst (250 mg) were charged in a 100 ml hydrothermal reactor. The reaction was carried out at 170 C for 8 h. The contents were allowed to cool to room temperature. Catalyst was separated by filtration from the reaction mixture. Then, the alcohol was removed from reaction mixture by distillation. The products were isolated by column chromatography (using pet ether:dichloromethane=1:1 and then with dichloromethane:methanol=95:5). The products were also analyzed by gas chromatography and identified by $^1$H NMR, FT-IR and GC-MS.

EXAMPLE 12

This example illustrates the reusability of the transester catalyst of the present invention in third recycle experiment for the preparation of dimethyl carbonate by transesterification of propylene carbonate with methanol. In a typical transesterification reaction, propylene carbonate (1.02 g; 10 mmol), methanol (100 mmol), three times used catalyst (250 mg) were charged in a 100 ml hydrothermal reactor. The reaction was carried out at 170° C. for 8 h. The contents were allowed to cool to room temperature. Catalyst was separated by filtration from the reaction mixture. Then, the alcohol was removed from reaction mixture by distillation. The products were isolated by column chromatography (using pet ether: dichloromethane=1:1 and then with dichloromethane:methanol=95:5). The products were also analyzed by gas chromatography and identified by $^1$H NMR, FT-IR and GC-MS. TABLE-2 lists the results of catalytic activity studies exemplified in EXAMPLES 6-12.

TABLE 2

Transesterification activity of double metal cyanide catalyst.

| Example No. | Oil or Carbonate | Alcohol | Oil conversio based on isolate glycerol yiel (mol %) | Transester selectivity (mol %) or yield (mol %) |
|---|---|---|---|---|
| Example 6 | Coconut oil | Methanol | 92.5 | Methyl caprilic ester (8.7%) + Methyl capric ester (5.8) + Methyl lauric este (45.6) + methyl myristic ester (18.4) + Methyl Palmitic ester (7.9%) + Methy (oleate + stereate + linoleate) esters (13.7) |
| Example 7 | Sunflower oil | Methanol | 92.3 | Methyl palmitic ester (6.8%) + Methyl (oleate + stereate + linoleate) ester (92.0) |
| Example 8 | Soybean oil | Methanol | 92.0 | Methyl esters (99%) |
| Example 9 | Margarine | Octanol | 91.0 | Octyl palmitate ester (13.8%) + Octyl (oleate + stereate + linoleate) ester (86.2%) |
| Example 10 | Propylene carbonate | Methanol | 86.6 | Dimethyl carbonate selectivity (92.4%); dimethyl carbonate isolated yiel (86.6%) |
| Example 11 | Propylene carbonate | Ethanol | — | Diethyl carbonate selectivity (87.3%); Diethyl carbonate yield (87.3%) |
| Example 12 | Propylene carbonate | Methanol | — | Dimethyl carbonate selectivity (93.0%); dimethyl carbonate isolated yiel (84.7%) |

ADVANTAGES

1. The process described above presents reusable, solid catalyst efficient for a range of transesterification reactions.
2. The catalyst is highly active even at moderate conditions and no leaching of metal ions from the solid catalyst into the reaction was observed.

We claim:
1. A transesterification catalyst having the general formula:

$$Zn_3M_2(CN)_n(ROH).xZnCl_2.yH_2O$$

wherein R is tertiary-butyl and M is a transition metal ion selected from Fe, Co and Cr, x varies from 0 to 0.5, y varies from 3-5 and n is 10 or 12, wherein the catalyst is formed by a method comprising:
 a) dissolving $ZnCl_2$ in a mixture of water and tertiary butanol,
 b) adding the above said solution obtained in step (a) to an aqueous solution of $K_4M(CN)_6$, under stirring,
 c) adding tri-block copolymer poly(ethyleneglycol)-block-poly(propylene glycol)-block-poly(ethyleneglycol) ($EO_{20}$-$PO_{70}$-$EO_{20}$; molecular weight of about 5800) dissolved in a mixture of tert.-butanol and water to the above said resultant mixture obtained in step (b), under stirring, at a temperature in the range of 50°-70° C., d. filtering the above said reaction mixture obtained in step (c) to obtain a solid product, followed by washing with a material consisting of distilled water in an amount of at least 500 ml and drying it at 20-50° C.; and e) activating the above said dried solid product, at a temperature in the range of 150-200° C. to obtained the desired transesterification catalyst.

2. A catalyst according to claim 1, wherein the catalyst comprises $Zn^{2+}$ and $Fe^{2+}$ ions bridged through cyanide groups.

3. A catalyst according to claim 1 having the following characteristics:

| | |
|---|---|
| Total surface area ($S_{BET}$) | 35-40 m²/g |
| External surface area ($S_{Exm.}$) | 22-25 m²/g |
| Micropore area | 14-18 m²/g |
| Average pore diameter | 3-5 nm |
| Total pore volume | 0.03-0.04 cc/g |
| % C-content | 23-25 |
| % H-content | 2.2-2.9 |
| % N-content | 17-18 |
| Morphology (SEM): | Spherical shaped particles. |

4. The transesterification catalyst according to claim 1, wherein in step (a) the concentration of tertiary butanol in water used is in the range of 20-30% (v/v).

5. The transesterification catalyst according to claim 1, wherein in step (c) the concentration of tri-block copolymer poly(ethyleneglycol)-block-poly(propylene glycol)-block-poly(ethyleneglycol) in a mixture of water and tertiary butanol used is in the range of 30-40% (w/v).

6. The transesterification catalyst according to claim 1, wherein in step (c) the ratio of tertiary butanol to water in a mixed solvent mixture used is in the range of 20:1 to 30:1 (v/v).

* * * * *